Figure 1:
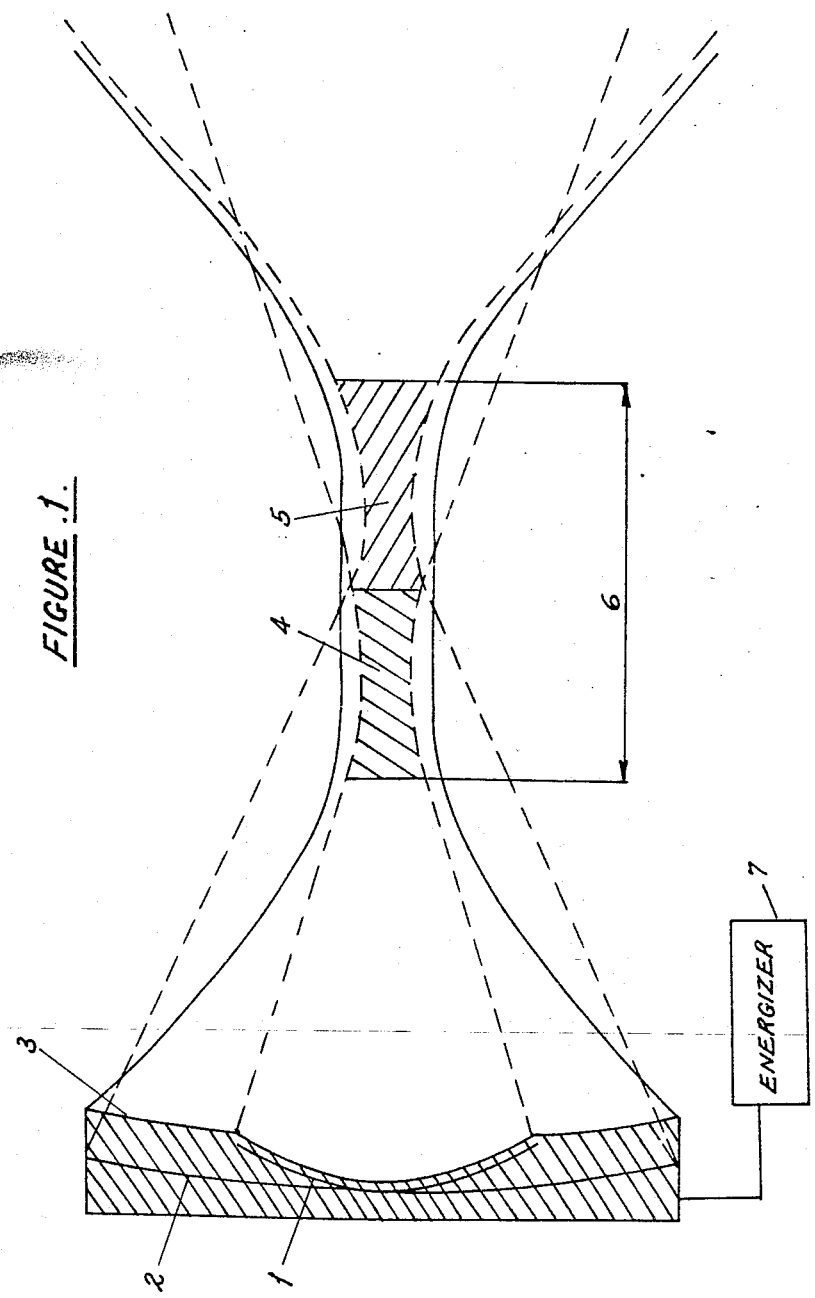

United States Patent
Kossoff

[11] 4,016,751
[45] Apr. 12, 1977

[54] ULTRASONIC BEAM FORMING TECHNIQUE

[75] Inventor: George Kossoff, Northbridge, Australia

[73] Assignee: The Commonwealth of Australia Care of the Department of Health, Phillip, Australia

[22] Filed: Sept. 29, 1975

[21] Appl. No.: 617,980

Related U.S. Application Data

[63] Continuation-in-part of Ser. No. 397,004, Sept. 13, 1973, abandoned.

[52] U.S. Cl. .......................................... 73/71.5 US
[51] Int. Cl.² ........................................ G01N 29/00
[58] Field of Search ............. 73/67.7, 67.8 R, 67.9, 73/71.5 US

[56] References Cited
UNITED STATES PATENTS

| | | | |
|---|---|---|---|
| 2,779,880 | 1/1957 | Malherbe | 73/71.5 US X |
| 3,166,731 | 1/1965 | Joy | 73/67.9 X |
| 3,251,219 | 5/1966 | Hertz et al. | 73/67.7 |
| 3,859,984 | 1/1975 | Langley | 73/67.7 X |

Primary Examiner—James J. Gill

[57] ABSTRACT

Apparatus for ultrasonic examination of objects, particularly in medical diagnostic examination, incorporates means for focusing portions of the beam of ultrasonic pulses generated by a transducer at a plurality of distances from the transducer to reduce the width of the beam over a large distance.

3 Claims, 2 Drawing Figures

ULTRASONIC BEAM FORMING TECHNIQUE

CROSS REFERENCE OF RELATED APPLICATION

This application is a Continuation-In-Part of my earlier patent application Ser. No. 397,004, filed Sept. 13, 1973, now abandoned.

This invention relates to the technique of ultrasonic echoscopy of objects and in particular to an extension of known techniques of ultrasonic echoscopy to provide more useful information concerning the examined objects. It is particularly, but not solely, directed to the more effective acquisition of data in medical diagnosis utilizing this technique.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, into the examined object where any acoustic impedance discontinuities in the object reflect and return some of the energy in the form of an echo. The echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed, for example, as a deflection of the base line or as an intensity change. In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar but not necessarily identical movement of the base line of the display. The magnitude of the echo is displayed as for a one dimensional display; for example, as a deflection of the base line or as an intensity change.

The technique of ultrasonic echoscopy is used in medical diagnosis to obtain information about the anatomy of patients. The application of the technique is now widely investigated and is described, for example, by D. E. Robinson in Proceeding of the Institution of Radio and Electronics Engineers Australia, Vol. 31, No. 11, pages 385–392, November, 1970; "The Application of Ultrasound in Medical Diagnosis". As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patients condition, however particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

If a pulse of ultrasound is propagated into a medium, echoes will be received at various time delays and these time delays will be proportional to the distances from the transducer producing the pulse to the interfaces provided the velocity of propagation is constant. In soft tissues found in the human body the velocity of sound is reasonably constant and pulsed ultrasound provides a convenient method of measuring the depth of a particular structure from the transducer face without inconvenience to the patient. This information can be used in a number of ways.

In the simplest form of display, "A mode", the echoes are presented as deflections of the trace of an oscilloscope in which distance is represented along the time axis. This mode is useful clinically when the source of the various echoes displayed can be positively identified. It is possible to measure the distance between two echoes, or between the energizing pulse and an echo, with accuracy but it may not be possible to identify the source of the echoes. It has been used to measure the size of the baby's head inside the uterus, the depth of the eye and the bladder and to locate the mid-line in the brain. Similar information may be displayed by use of the "B mode" in which the echoes are presented as a brightening or intensity modulation of the time-base trace.

If the interface of interest is moving, its position may be plotted with time ("M mode") by using the B mode presentation and allowing the time base to be swept at right angles to its direction so as to display the movements of the interface echo backwards and forwards along the time base. This is used to demonstrate the pulsatile movements of various parts of the heart and brain. If the B mode is used but the trace on the screen is made to represent the line of sight of the transducer and then the transducer is scanned around the patient and the time base line on the screen made to follow, a two-dimensional plot of impedance discontinuities is obtained. Two dimensional visualization has been used in the pregnant uterus, abdomen, eye and breast.

Coupling from the transducer to the patient may be achieved by skin contact or by use of a water delay bath. If a water delay bath is used the distance between the transducer and the skin surface must be greater than the largest depth of penetration to be used, to avoid ambiguity due to multiple reflection. In general the skin contact scan results in greater comfort for the patient and echograms of less clarity while the water delay scan gives less patient comfort and better quality echograms.

In many ultrasonic applications it is desirable to have a narrow ultrasonic beam over a distance which is large compared to the dimensions of the transducer used to generate the beam. An example of this occurs in an ultrasonic pulse echo examination where the width of the ultrasonic examining beam determines the lateral resolution of the technique so that a narrow beam is desired over the whole penetration of the energy into the examined object.

The width of an ultrasonic beam may be narrowed by focusing or shaping the beam either (i) by a lens or a mirror in a manner similar to focusing in optics, (ii) by a curved surface on a transducer, or (iii) by a multielement transducer where the elements of the transducer are energized at progressively different times to generate the desired shape.

If the beam is shaped so that the whole wavefront is focused at a single distance from the transducer, the beam is narrowed on either side of the focus by a factor which depends on the degree of the curvature of the wavevfront. If a highly curved wavefront is used a large reduction in width is obtained over a short distance while if a less curved wavefront is used a smaller reduction is obtained over a large distance. Such simple focusing is also described in Kossoff et al "Ultrasonic Two-Dimensional Visulization for Medical Diagnosis", JASA Volume 44, No. 5, November 1968, PP 1310–1318.

It is an object of the present invention to provide apparatus and a method whereby the width of the beam from a single transducer can be reduced over an extended distance.

According to the present invention, there is provided a method of reducing the width of a beam of ultrasonic energy, generated by a transducer, over an extended distance, comprising:

focusing a first portion of said beam at a first distance from said transducer;

simultaneously focusing at least one additional portion of said beam, coaxial with said portion, at a distance from said transducer different from said first distance;

thereby to produce a coaxial composite beam having a multi-curved converging wavefront and concentrating said energy in a line of focus.

This invention also provides apparatus for reducing the width of a beam of ultrasonic energy, generated by a transducer, over an extended distance, comprising:

means for focusing a first portion of said beam at a first distance from said transducer; and means for simultaneously focusing at least one additional portion of said beam, coaxial with said portion, at a distance from said transducer different from said first distance;

whereby a coaxial composite beam having a multi-curved converging wavefront is produced and said energy is concentrated in a line of focus.

Figure 2:
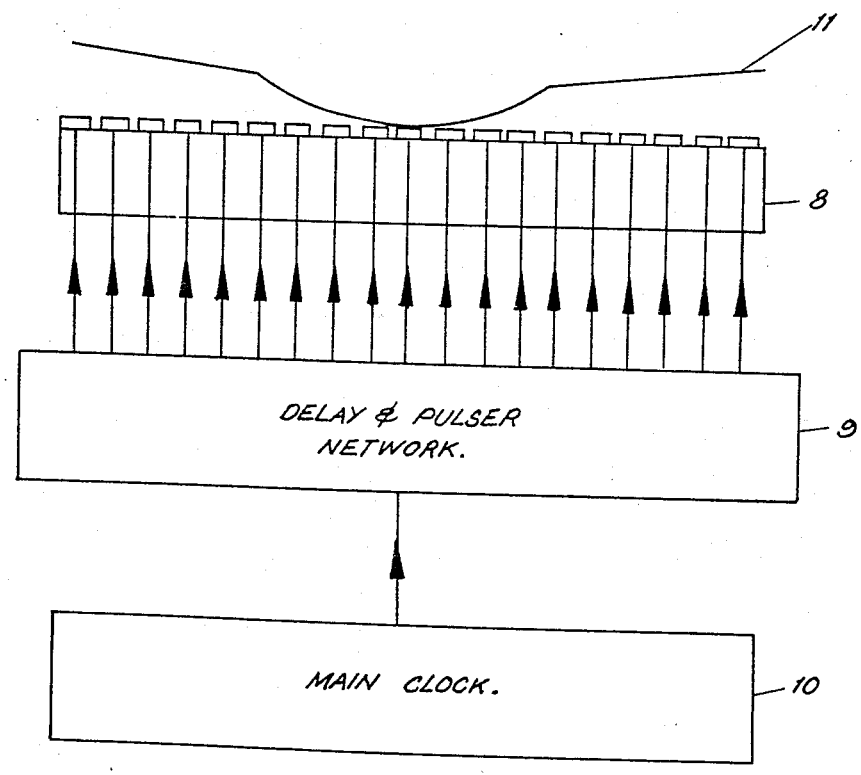

Other objects and features of the invention will be apparent from the accompanying drawings in which:

FIG. 1 schematically depicts the focusing of wave fronts of various transducers, including the formation of a multi-curved wavefront in accordance with the present invention; and FIG. 2 shows a schematic layout of a multi-element array transducer and electronic delay elements to produce an identical wavefront to that generated in FIG. 1.

FIG. 1 illustrates three transducers and the beams produced thereby - a smaller diameter, more curved transducer show schematically at 1, the larger diameter less curved transducer shown schematically at 2, and the double curved transducer of the present embodiment 3, the inner portion of which is identical to transducer 1 and the outer portion of which is identical to the corresponding portion of transducer 2. As illustrated in this Figure, a single curved transducer such as 1 would generate a narrow beam over a short distance 4 about its focus while a single curved transducer such as 2 would generate a narrow beam over a short distance 5. On being energized by energizer 7, double-curved transducer 3 generates a double curved wavefront, the inner portion of which focuses the beam over the short distance 4. Because the focusing properties of a wave front are determined mostly by the outer dimensions, the outer portion of transducer 3 generates a beam which is similar to that which would be generated by a transducer such as 2, i.e., it creates a narrow beam over distance 5. Thus, the double curved wavefront generated by transducer 3 generates a narrow beam over the combined distance 6. It will therefore be apparent that wavefront produced by transducer 3 is shaped so that different portions of the wavefront are focused simultaneously at different distances from the transducer.

FIG. 2 shows an alternative layout consisting of an array of transducer elements 8 which are energised by electronic delay and pulser network 9. This network consists of a delay element and pulse generator for each transducer array element. Delay elements and pulse generators are well known in the art. The delay of each delay element is adjusted so that when the delay elements are energised by a pulse from the main clock 10, transducer array elements 8 are pulsed by the pulse generators 9 such that the wavefront 11 produced is similar to that produced by the multi-curved transducer shown in FIG. 1. In order to obtain a wavefront of this form, the outer elements of transducer array 8 must be pulsed first (no delay), the more central ones next (small delay) and the central element last (maximum delay). The transducer array 8 may be a linear array or may be circularly symmetric with an axis of symmetry passing through the central element. The elements of transducer array 8 may be equal in size or they may be of varying size to reduce the number of elements required in the delay and pulse network 9.

In FIG. 1 of the foregoing description, the focusing of the beam in accordance with the invention is achieved by use of a double curved transducer, however, it is to be understood that transducers which have more than two curvatures may also be employed to produce a multi-curved wave front to generate narrow beams of ultrasonic pulses over extended distances. Further, it will be understood that mechanical focusing may be achieved by the use of transducers having curved surfaces, by lenses or mirrors, or by a combination of any two or more of these focusing means. Thus, double-curved transducer 3 shown in FIG. 1 may comprise a relatively small diameter curved central transducer surface portion and a relatively larger diameter curved outer transducer surface portion, the radius of curvature of said central surface portion being smaller than the radius of curvature of said outer surface portion. Preferably, however, transducer 3 comprises a double-curved lens formed on a planar transducer surface in a manner similar to that described in Kossoff et al (supra) for simple focusing by means of a lens.

From the foregoing description it will therefore be appreciated that the present invention utilises a multi-curved wavefront to reduce the width of the beam of ultrasonic pulses generated by a transducer over an extended distance. While the invention has been described with reference to an illustrative embodiment, it will generally be understood by those skilled in the art that various changes may be made and equivalents be substituted for elements thereof without departing from the true spirit and scope of the invention.

The claims defining the invention are as follows:

1. Apparatus for reducing the width of a beam of ultrasonic energy, generated by a transducer, over an extended distance, comprising:

means for focusing a first portion of said beam at a first distance from said transducer; and means for simultaneously focusing at least one additional portion of said beam, coaxial with said first portion, at a distance from said transducer different from said first distance;

whereby a coaxial composite beam having a multi-curved converging wavefront is produced and said energy is concentrated in a line of focus;

wherein said means for focusing the portions of said beam at different distances from the transducer comprise a multi-curved surface on said transducer.

2. Apparatus for reducing the width of a beam of ultrasonic energy, generated by a transducer, over an extended distance, comprising:

means for focusng a first portion of said beam at a first distance from said transducer; and means for simultaneously focusing at least one additional portion of said beam, coaxial with said first portion, at a distance from said transducer different from said first distance;

whereby a coaxial composite beam having a multi-curved converging wavefront is produced and said energy is concentrated in a line of focus;

wherein said transducer comprises a multi-element array, and said means for focusing the portions of said beam at different distances from the transducer comprise means for energising the elements of said array with varying delay periods.

3. Apparatus for reducing the width of a beam of ultrasonic energy, generated by a transducer, over an extended distance, comprising:

a multi-curved surface on said transducer for focusng a first portion of said beam at a first distance from said transducer and simultaneously focusing at least one additional portion of said beam at a distance from said transducer different from said first distance, whereby a composite beam having a multi-curved wavefront is produced and said energy is concentrated in a line of focus;

said multi-curved surface comprising a relatively small diameter curved central surface portion and a relatively larger diameter curved outer surface portion, the radius of curvature of said central surface portion being smaller than the radius of curvature of said outer surface portion.

* * * * *